(12) United States Patent
Aubanel et al.

(10) Patent No.: US 7,289,216 B2
(45) Date of Patent: Oct. 30, 2007

(54) STATION FOR INSPECTING THE PAINTING OF MOTOR VEHICLE PARTS

(75) Inventors: Laurent Aubanel, Villette sur Ain (FR); Laurent Dam, Priay (FR); Patrick Magnier, Parmilieu (FR)

(73) Assignee: Compagnie Plastic Omnium, Lyons (FR)

( * ) Notice: Subject to any disclaimer, the term of this patent is extended or adjusted under 35 U.S.C. 154(b) by 165 days.

(21) Appl. No.: 10/894,423

(22) Filed: Jul. 19, 2004

(65) Prior Publication Data

US 2006/0012801 A1 Jan. 19, 2006

(51) Int. Cl.
*G01J 3/46* (2006.01)
*B05C 11/00* (2006.01)

(52) U.S. Cl. .................. 356/402; 356/600; 356/73; 118/712; 901/47

(58) Field of Classification Search ............... 356/600, 356/73, 402, 601; 118/712; 901/47
See application file for complete search history.

(56) References Cited

U.S. PATENT DOCUMENTS

| | | | | |
|---|---|---|---|---|
| 4,498,414 A | * | 2/1985 | Kiba et al. | 118/663 |
| 4,714,044 A | * | 12/1987 | Kikuchi et al. | 118/314 |
| 4,833,325 A | * | 5/1989 | Torii et al. | 250/584 |
| 5,726,705 A | * | 3/1998 | Imanishi et al. | 348/92 |
| 5,774,227 A | * | 6/1998 | Oei | 356/430 |
| 5,835,223 A | * | 11/1998 | Zwemer et al. | 356/600 |
| 6,266,138 B1 | * | 7/2001 | Keshavmurthy | 356/237.2 |
| 6,384,421 B1 | * | 5/2002 | Gochar, Jr. | 250/559.46 |
| 6,528,109 B1 | * | 3/2003 | Filev et al. | 427/9 |
| 6,559,655 B1 | * | 5/2003 | Rosenthal et al. | 324/634 |
| 6,936,106 B2 | * | 8/2005 | Filev et al. | 118/665 |
| 7,046,348 B2 | * | 5/2006 | Fleischer | 356/73 |
| 2005/0046871 A1 | * | 3/2005 | Martinschledde et al. | 356/601 |
| 2005/0173660 A1 | * | 8/2005 | Umemura | 250/589 |
| 2005/0248774 A1 | * | 11/2005 | Herrmann et al. | 356/601 |

FOREIGN PATENT DOCUMENTS

WO WO0227298 * 4/2002

OTHER PUBLICATIONS

Christine Connolly, Robotic colour measurement of metallic and pearlescent paint, Industrial Robot: An International Journal, vol. 31, No. 3, 2004 pp. 258-260.*
G. Matthies, Contactless colour measurement, Qualitaet und Zuverlaessigkeit, V47, N8, pp. 830-831, 2002.*
Frank De Pascalis, Automated quality analysis (AQUA) in varnishing, Europ. Automotive Coating, 11th DFO Automotice-Conf,Dt. Forschungsges. f. Oberflaechenbehandlung, Conf. Papers, Maastricht, NL May 4-5, 2004.*
Carflash Online multiangle color measuring device, http://www.laser2000.fr/medias/INSTRUMENTATION/Optronik/Carflash_brochure_eng.pdf?PHPSESSID=b7c7455e68a0fd03edb53b66ef1d499b.*

* cited by examiner

*Primary Examiner*—Layla G. Lauchman
*Assistant Examiner*—David H. Parker
(74) *Attorney, Agent, or Firm*—James R. Williams

(57) ABSTRACT

A station for inspecting the painting of motor vehicle bodywork parts, the station including an optical measuring apparatus and means for attenuating vibration of the moving parts.

13 Claims, 3 Drawing Sheets

STATION FOR INSPECTING THE PAINTING OF MOTOR VEHICLE PARTS

The present invention relates to a station for inspecting the painting of motor vehicle bodywork parts.

BACKGROUND OF THE INVENTION

It is known that those bodywork parts which are painted off the main vehicle assembly line must be painted in compliance with very precise criteria for color and surface state so that such parts have the same appearance as the remainder of the bodywork which is painted as a body.

It is also known that the settings of a painting line can drift as a function of various factors, such as, for example: humidity, ambient temperature, and atmospheric pressure; and that it is essential to monitor parts as they leave the painting line, at least for quality control purposes, and possibly also for making consequential adjustments to the settings of the line.

For this purpose, it is known to use an optical measuring apparatus such as that sold under the reference CARFLASH by the US supplier X-RITE.

That apparatus is disposed at the end of the painting line on a "stop-and-go" station, i.e. a station at which parts being inspected make a pause during which the measurement is performed, after which they continue with their progress along the line.

Until now, stations for inspecting the painting of motor vehicle parts have always been of the stop-and-go type, since the measuring apparatus is known to be highly sensitive to vibration, and any displacement of the parts along the line inevitably leads to considerable amounts of vibration in the parts.

Indeed, that is the method of using the measuring apparatus that is recommended by its manufacturer.

OBJECTS AND SUMMARY OF THE INVENTION

However, there exists a need for a solution that makes it possible to inspect parts without stopping them, so as to be suitable for being fitted to painting lines where painting is performed on parts that are moving.

The present invention seeks to propose a solution enabling that object to be achieved.

The present invention provides an inspection station for inspecting the painting of motor vehicle bodywork parts, the station including an optical measuring apparatus, wherein the apparatus is mounted on a tracker robot which moves it along the path of a part moving while measurement is taking place, and wherein the inspection station includes at least a portion of a conveyor for parts, which portion is provided with means for attenuating vibration of the moving parts.

By means of the invention, the parts are prevented from vibrating while they are going past the inspection station so as to enable the surface state of their painting to be measured by the optical measuring apparatus which is moving parallel with the parts so as to be substantially stationary relative to them for the time needed to take the measurement.

In various embodiments of the invention, the vibration can be attenuated by the following means which can be taken singly or in combination:

for parts being conveyed by poles carried at their bases by moving carriages, a slideway is provided along the painting inspection station for receiving the free top ends of the poles and for guiding them parallel to the path of the carriages so as to prevent them from rocking transversely with rolling motion. This embodiment is advantageous since the inventors have been able to identify that transverse vibrations of the free top end of a pole are a significant factor in the optical measuring apparatus taking poor measurements;

when conveying is provided by poles as described above, holding members for holding the free top ends of the poles are arranged above the carriages, and are driven parallel to the carriages so as to accompany the travel of the poles, which poles are thus held at both top and bottom ends, and are prevented from vibrating. The holding members may, for example, be in the form of cones placed on the top ends of the poles, and they may exert a small amount of vertical pressure thereon, the cones being carried by an endless belt or chain which advances at the travel speed of the carriages;

when the parts are conveyed by carriages running on rails, provision is made for a portion of the rails to be constituted by a not very adherent material, such as polytetrafluoroethylene (PTFE). The low adhesion of the material makes it easier to clean, which is advantageous since the inventor has identified that a non-negligible fraction of the vibration comes from paint dust that has been deposited on the rails. In an improved variant of this embodiment, an active device (e.g. a blower) continuously removes dust that becomes deposited on the portion of the rails constituted by the not very adherent material;

when conveying is performed as described above, a portion of rail is provided that does not include any joints so that the carriages going past the inspection station are not subjected to vibration due to crossing a gap zone between two consecutive rail portions. This embodiment and the preceding embodiment can be implemented by covering the rails of the conveyor in a layer of not very adherent material over a length that corresponds to that of the inspection station; and when conveying is performed by wheeled carriages, raised rails are provided for the carriages in the region of the inspection station so that during inspection the carriages cease to be carried by the wheels that carry them through the painting line and that are generally dirtied by dust that interferes with smooth running. A raised rail may be constituted by a sliding strip which supports a sliding bearing surface formed on each carriage, or by a running strip for receiving special wheels carried by the carriages. Conversely, the sliding rail may be constituted by wheels carrying the carriages via running strips formed on the carriages. In any event, a portion of the carriage co-operating with the raised rails needs to be located at a position on the carriage that is sufficiently well protected to avoid receiving too much paint dust on passing through the painting line.

BRIEF DESCRIPTION OF THE DRAWINGS

The invention will be better understood on reading the following description given purely by way of example and made with reference to the accompanying drawings, in which.

MORE DETAILED DESCRIPTION

Figure 1:
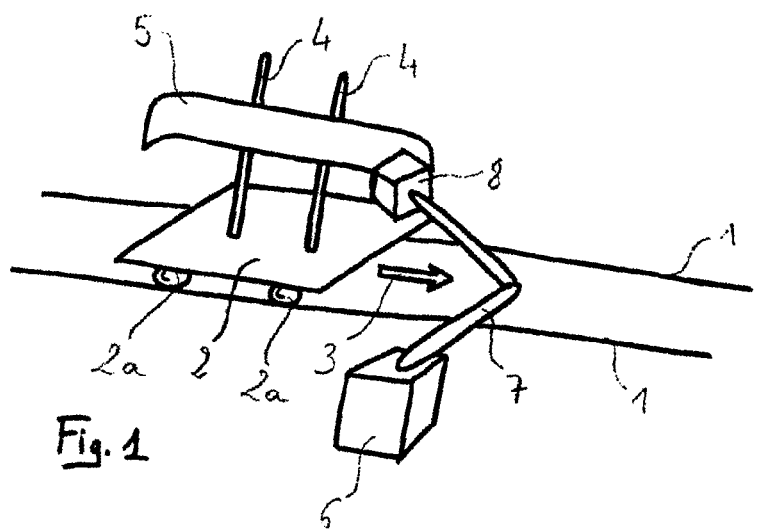
FIG. 1 is a perspective view of a painting inspection station situated at the outlet from a painting line.
Figure 2:
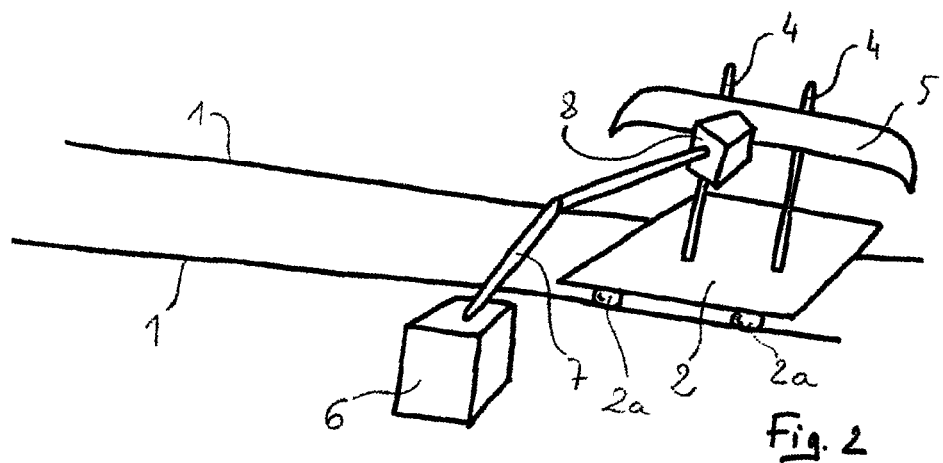
FIG. 2 is a view analogous to FIG. 1 showing the inspection station at a later stage during inspection.

FIGS. 1 and 2 show an inspection station situated beside the rails 1 of a conveyor which causes carriages 2 to travel through a painting line (not shown).

This painting line differs from a line for painting unpainted bodies since the bodywork parts are carried individually on poles 4 that are fixed to the carriages 2.

Because the carriages 2 run on the rails 1 via wheels 2a, the travel of the bodywork parts 5 is accompanied by a large amount of vibration.

The inspection station proper is constituted by a robot 6 provided with a manipulator arm 7 having a measuring apparatus 8 at its end for taking measurements on the bodywork parts 5 moving in the direction of arrow 3.

The movements of the measuring apparatus 8 driven by the manipulator arm 7 are programmed in a control apparatus (not shown) so that the measuring apparatus 8 tracks the path of each bodywork part 5, as can be seen in FIG. 2.

The measuring apparatus 8 and the bodywork parts 5 describe movements that are identical, ignoring vibration, such that, during the time interval corresponding to taking a measurement, the measuring apparatus 8 can be considered as being stationary relative to the bodywork parts 5, ignoring vibration.

Amongst the kinds of vibration that are the most troublesome for taking measurements properly, the rolling movement of the poles 4, i.e. rocking transversely relative to the travel direction of the carriages, constitutes a significant cause of poor measurement.

Figure 3:
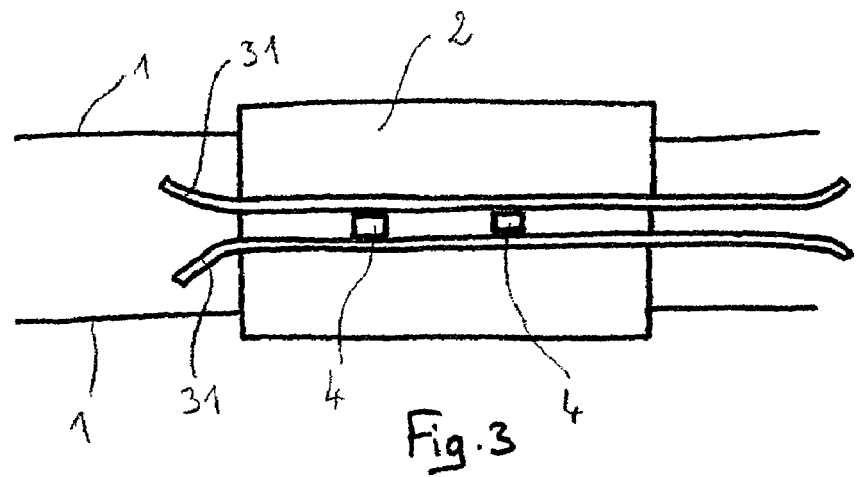
FIG. 3 is a plan view of an inspection station in a first embodiment of the invention.

That is why, in a first embodiment as shown in FIG. 3, a slideway is provided above the carriage, situated at the same height as the top ends of the poles 4. The slideway is constituted by two bars 31 which extend parallel to each other and parallel to the rails 1, except at the entrance to the slideway where the two bars 31 diverge so as to form a converging inlet to facilitate inserting the top ends of the poles 4 into the slideway, and except at the outlet from the slideway, where the two bars 31 diverge so as to release the poles gently.

So long as the poles 4 are maintained inside the slideway, which is of a width close to the width of the poles, the poles are prevented from vibrating transversely, thereby limiting the vibration of the bodywork parts 5 and enabling measurements to be taken properly by the measuring apparatus 8, which for reasons of clarity is omitted from FIGS. 3 to 7.

Figure 4:
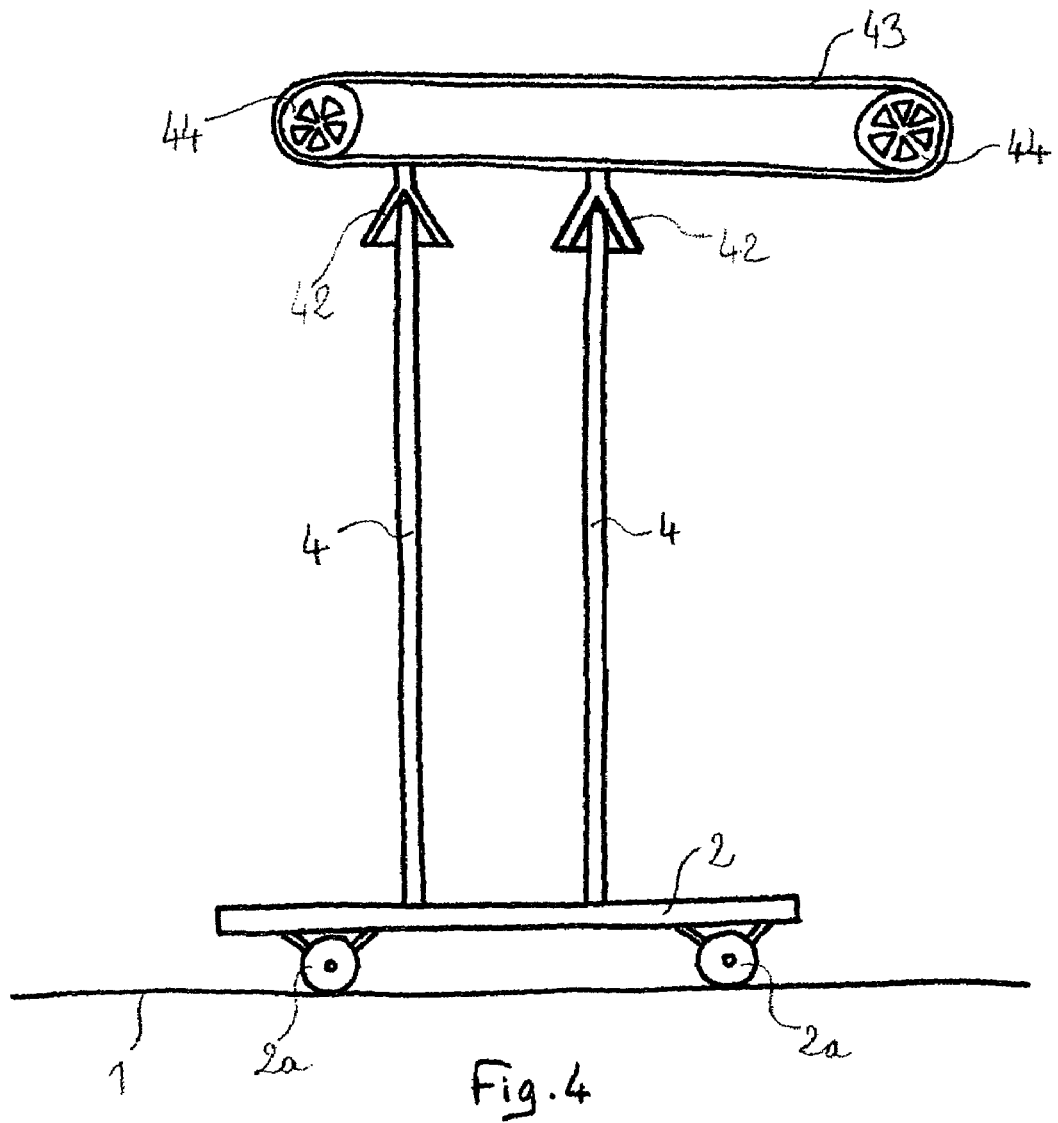
FIG. 4 is an elevation view of an inspection station in a second embodiment of the invention.

The inspection station in the second embodiment of the invention, shown in FIG. 4, is likewise provided with means for preventing the poles 4 from vibrating. Unlike the first embodiment, these means prevent the poles from moving not only in the transverse direction but also prevent them from vibrating or traveling in unwanted manner in any other direction, including to a small extent in the vertical direction.

For this purpose, pole-blocking means are constituted by cones 42 that are carried on an endless belt 43 wound on two rollers 44 which are rotated so as to impart a travel speed to the endless belt 43 that is identical to the speed of the carriage 2.

Thus, by providing good synchronization between the arrival of a carriage and the positions of the cones, the cones cover the top ends of the poles 4 and prevent them from moving relative to the endless belt 43. The poles 4 are thus held at their bottom ends by the carriage 2 and at their top ends by the endless belt 43, thereby preventing them from performing any rocking movement in any direction.

In addition, the cones exert a small amount of downwardly-directed pressure on the poles, merely by the rollers 44 being positioned at the appropriate height relative to the poles, so that the wheels 2a of the carriage are pressed down against the rails 1, thereby also eliminating vertical vibration due to running on dust.

In a variant that is not shown, resilient return means are interposed between the shafts (not shown) of the rollers and the structure supporting them (not shown), or between the cones 42 and the endless belt 43, so as to maintain sufficient pressure on the poles and so as to enable the device to adapt to poles of slightly different heights, as is generally the case between different carriages on a painting line.

Figure 5:
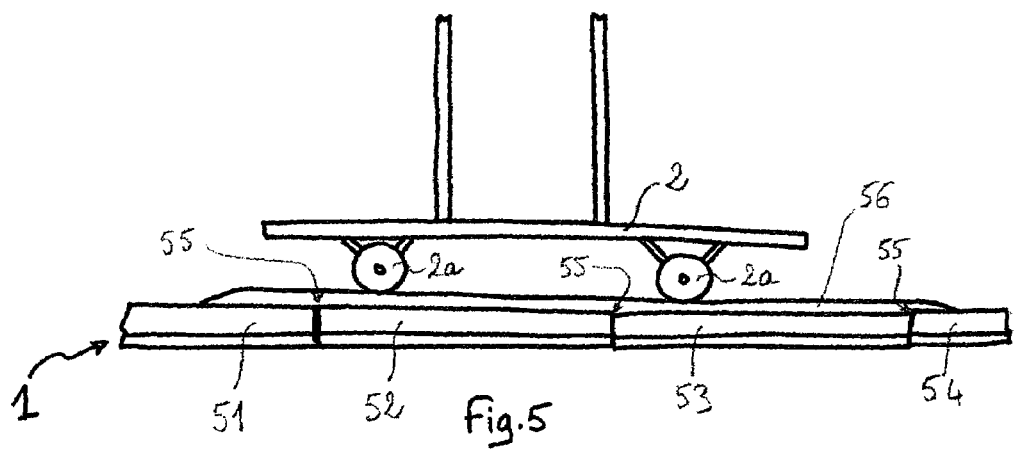
FIG. 5 is an elevation view of an inspection station in a third embodiment of the invention.

In the third embodiment, shown in FIG. 5, the rail 1 is made in conventional manner by a plurality of bars 51, 52, 53, 54 in end-to-end abutment. Between two successive bars, a gap zone 55 leads to jolting of the carriages 2 as their wheels 2a cross the gap, thereby generating vibration in the bodywork parts.

In order to remedy this non-uniformity of the rail 1, a layer 56 of a material suitable for constituting a running surface for the wheels 2a covers the bars 51, 52, 53, and 54 and also covers the gap zones 55 between them over the entire length of the inspection station.

Thus, while the measuring apparatus 8 (not shown in this figure) is taking measurements, the wheels 2a are running on a running surface that is smooth and continuous.

In addition, the material is advantageously a not very adherent material such as PTFE, thus enabling it to be cleaned easily in order to remove any dust that might become deposited thereon.

In a variant (not shown), an active device for cleaning the layer of material 46 is provided for the purpose of continuously removing any dust that becomes deposited thereon. This device may also perform rapid cleaning of the wheels 2a upstream from the inspection station.

Figure 6:
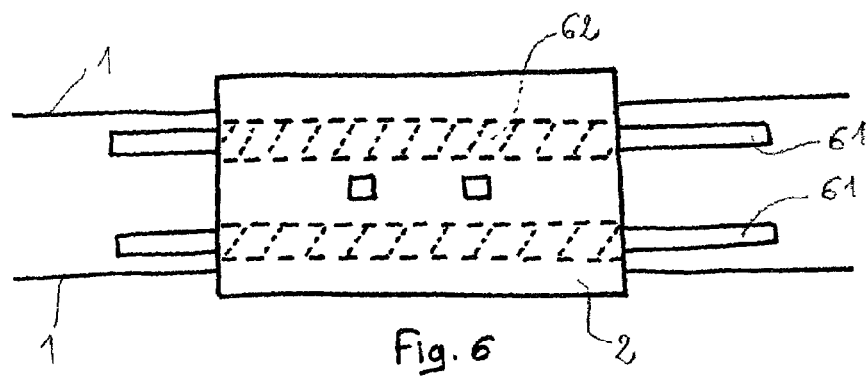
FIG. 6 is a plan view of an inspection station in a fourth embodiment of the invention.
Figure 7:
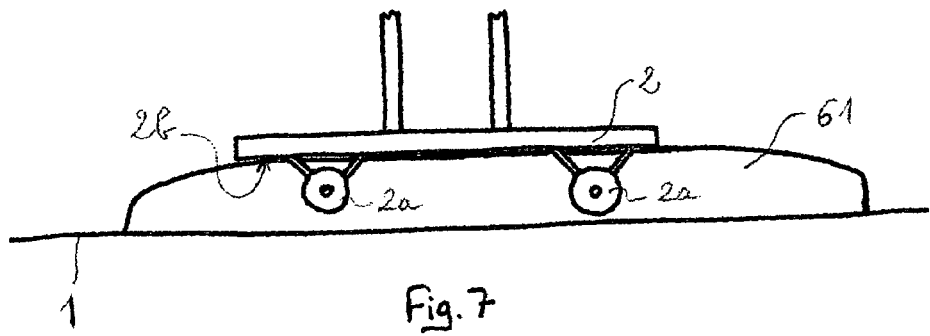
FIG. 7 is an elevation view of the FIG. 6 inspection station.

In the fourth embodiment of FIGS. 6 and 7, the means for attenuating the vibrations of the parts are constituted by raised rails 61 disposed between the rails 1 and in parallel therewith.

Each raised rail 61 is designed to bear against a sliding zone 62 provided on the bottom face 2b of the carriage 2.

As can be seen in FIG. 7, the raised rails are at a height such that when the carriage is being carried by said raised rails, the wheels 2a are lifted off the rails 1.

The leading and trailing ends of the raised rails are naturally chamfered or rounded so as to make it easier to raise and lower the carriages.

As in the preceding embodiment, an active cleaning device may be provided for removing any dust that might become deposited on the raised rails. A like cleaning device may also clean the sliding surfaces 62 upstream from the inspection station.

Naturally, the embodiments described above are not limiting in any way, and may receive any desirable modification without thereby going beyond the ambit of the invention.

What is claimed is:

1. An inspection station for inspecting the painting of motor vehicle bodywork parts, the station including an optical measuring apparatus, wherein the apparatus is mounted on a tracker robot which moves the apparatus along a path of a part moving while measurement is taking place, and wherein the inspection station includes at least a portion of a conveyor for parts, which portion is provided with means for attenuating vibration of the moving parts.

2. A station according to claim 1, the parts being conveyed by poles carried at their bases by moving carriages, in which a slideway is provided along the paint inspection station for receiving the free top ends of the poles and for guiding them parallel to the path of the carriages so as to prevent them from rocking transversely with rolling motion.

3. A station according to claim 1, the parts being conveyed by poles carried at their bases by moving carriages, in which holding members for holding the free top ends of the poles are arranged above the carriages, and are driven parallel to the carriages so as to accompany the travel of the poles, which poles are thus held at both top and bottom ends, and are prevented from vibrating.

4. A station according to claim 1, the parts being conveyed by carriages running on rails, wherein a portion of the trails is made of a not very adherent material such as PTFE.

5. A station according to claim 1, conveying being performed by carriages running on rails, in which a portion of the rails does not include any joints, so that the carriages going past the inspection station are not subjected to vibration due to crossing a gap zone between two consecutive rail portions.

6. A station according to claim 4, in which the rails are covered in a layer of not very adherent material over a length that corresponds to the length of the inspection station.

7. A station according to claim 1, conveying being performed by wheeled carriages, in which raised rails are provided for raising the carriages in the region of the inspection station so that during inspection the carriages cease to be carried by the wheels that have carried the carriages through the painting line.

8. An inspection station for inspecting the painting of motor vehicle bodywork parts, the station including an optical measuring apparatus, wherein the apparatus is mounted on a tracker robot which moves the apparatus along a path of a part moving while measurement is taking place, and wherein the inspection station includes at least a portion of a conveyor for parts, which portion is provided with means for attenuating vibration of the moving parts, the parts being conveyed by poles carried at their bases by moving carriages, in which a slideway is provided along the paint inspection station for receiving the free top ends of the poles and for guiding the poles parallel to the path of the carriages so as to prevent the poles from rocking transversely with rolling motion.

9. An inspection station for inspecting the painting of motor vehicle bodywork parts, the station including an optical measuring apparatus, wherein the apparatus is mounted on a tracker robot which moves the apparatus along a path of a part moving while measurement is taking place, and wherein the inspection station includes at least a portion of a conveyor for parts, which portion is provided with means for attenuating vibration of the moving parts, the parts being conveyed by poles carried at their bases by moving carriages, in which holding members for holding the free top ends of the poles are arranged above the carriages, and are driven parallel to the carriages so as to accompany the travel of the poles, which poles are thus held at both top and bottom ends, and are prevented from vibrating.

10. An inspection station for inspecting the painting of motor vehicle bodywork parts, the station including an optical measuring apparatus, wherein the apparatus is mounted on a tracker robot which moves the apparatus along a path of a part moving while measurement is taking place, and wherein the inspection station includes at least a portion of a conveyor for parts, which portion is provided with means for attenuating vibration of the moving parts, the parts being conveyed by carriages running on rails, wherein a portion of the rails is made of a not very adherent material.

11. An inspection station for inspecting the painting of motor vehicle bodywork parts, the station including an optical measuring apparatus, wherein the apparatus is mounted on a tracker robot which moves the tracker robot along a path of a part moving while measurement is taking place, and wherein the inspection station includes at least a portion of a conveyor for parts, which portion is provided with means for attenuating vibration of the moving parts, the conveyor comprising carriages running on rails, in which a portion of the rails does not include any joints, so that the carriages going past the inspection station are not subjected to vibration due to crossing a gap zone between consecutive rail portions.

12. An inspection station for inspecting the painting of motor vehicle bodywork parts, the station including an optical measuring apparatus, wherein the apparatus is mounted on a tracker robot which moves the apparatus along a path of a part moving while measurement is taking place, and wherein the inspection station includes at least a portion of a conveyor for parts, which portion is provided with means for attenuating vibration of the moving parts, the conveyor comprising wheeled carriages, in which raised rails are provided for raising the carriages in the region of the inspection station so that during inspection the carriages cease to be carried by the wheels that have carried the carriages through the painting line.

13. The inspection station of claim 10, wherein the not very adherent material includes PTFE.

* * * * *